US012653551B2

(12) United States Patent
McDowell

(10) Patent No.: US 12,653,551 B2
(45) Date of Patent: Jun. 16, 2026

(54) SURGICAL DRILL FOR CRANIOSYNOSTOSIS AND ENDOSCOPIC PROCEDURES

(71) Applicant: UNIVERSITY OF PITTSBURGH—OF THE COMMONWEALTH SYSTEM OF HIGHER EDUCATION, Pittsburgh, PA (US)

(72) Inventor: Michael McDowell, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 18/843,429

(22) PCT Filed: Jan. 9, 2023

(86) PCT No.: PCT/US2023/010400
§ 371 (c)(1),
(2) Date: Sep. 3, 2024

(87) PCT Pub. No.: WO2023/183067
PCT Pub. Date: Sep. 28, 2023

(65) Prior Publication Data
US 2025/0169829 A1     May 29, 2025

Related U.S. Application Data

(60) Provisional application No. 63/321,910, filed on Mar. 21, 2022.

(51) Int. Cl.
*A61B 17/16*          (2006.01)

(52) U.S. Cl.
CPC ...... *A61B 17/1695* (2013.01); *A61B 17/1615* (2013.01); *A61B 17/1628* (2013.01)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS 3,448,592 A * 6/1969 Von Tersch ............. B25B 17/00
                                                                66/149 R
5,304,191 A * 4/1994 Gosselin ............ A61B 17/1695
                                                                30/276
(Continued)

FOREIGN PATENT DOCUMENTS

CA        3086691 A1    7/2019
CN        107951534 A * 4/2018    ......... A61B 17/1626
(Continued)

OTHER PUBLICATIONS

Bykowski et al., "Spring-Mediated Cranioplasty for Treatment of Sagittal Synostosis," Neurosurgical Aspects of Craniosynostosis, Springer Nature, Jan. 2025, Chapter 41, pp. 507-517.
(Continued)

*Primary Examiner* — Eric S Gibson
(74) *Attorney, Agent, or Firm* — Fish & Richardson P.C.

(57)          ABSTRACT

A surgical drill system for use with a drill bit includes a base and a drill head positioned forward of the base which is operatively connected to the base. The drill head includes a drill bit interface to which a shaft of the drill bit is attachable so that an axis of the shaft of the drill extends at an angle to an orientation of the drill head at the position of the drill bit interface. The surgical drill system further includes a drive system in operative connection with the drill bit interface (Continued)

which is configured to rotate the drill bit about the axis of the shaft of the drill bit when connected to the interface.

17 Claims, 13 Drawing Sheets

(58) Field of Classification Search
CPC ............ A61B 17/1622; A61B 17/1624; A61B 17/1626; A61B 17/1628; A61B 17/1631; A61B 17/1655; A61B 17/1657; A61B 17/1659; A61B 17/1662; A61B 17/1671; A61B 17/1673; A61B 17/1682; A61B 17/1686; A61B 17/1688; A61B 17/1695; A61B 2017/1602
See application file for complete search history.

(56) References Cited

U.S. PATENT DOCUMENTS

| | | | | |
|---|---|---|---|---|
| 5,628,748 | A * | 5/1997 | Vicari | A61B 17/1695 606/176 |
| 7,207,233 | B2 * | 4/2007 | Wadge | B25F 5/02 74/412 R |
| 7,648,513 | B2 | 1/2010 | Green et al. | |
| 7,922,720 | B2 | 4/2011 | May et al. | |
| 9,080,611 | B2 * | 7/2015 | Sander | F16D 3/207 |
| 9,446,455 | B2 * | 9/2016 | Gagnon | E03F 7/12 |
| 9,470,297 | B2 * | 10/2016 | Aranyi | A61B 17/0686 |
| 9,597,093 | B2 * | 3/2017 | Mcclymont | F16D 3/265 |
| 10,561,427 | B2 * | 2/2020 | Weitzman | A61B 17/1633 |
| 10,779,952 | B2 * | 9/2020 | Gunther | A61B 17/1659 |
| 11,844,534 | B2 * | 12/2023 | Bhatia | A61B 17/1642 |
| 11,911,233 | B2 * | 2/2024 | Patel | A61B 17/7082 |
| 2005/0165420 | A1 * | 7/2005 | Cha | A61B 17/1633 606/150 |
| 2006/0195194 | A1 * | 8/2006 | Gunther | A61B 17/15 606/80 |
| 2006/0229624 | A1 * | 10/2006 | May | A61B 17/32002 606/79 |
| 2007/0282344 | A1 * | 12/2007 | Yedlicka | A61B 17/1671 606/80 |
| 2009/0023988 | A1 * | 1/2009 | Korner | A61B 17/1624 600/114 |
| 2009/0088770 | A1 | 4/2009 | Kim et al. | |
| 2010/0057087 | A1 * | 3/2010 | Cha | A61B 17/1633 606/80 |
| 2010/0179557 | A1 * | 7/2010 | Husted | A61B 17/32002 600/300 |
| 2012/0143195 | A1 * | 6/2012 | Sander | F16D 3/207 464/106 |
| 2014/0058394 | A1 * | 2/2014 | Siegal | A61B 17/1671 606/80 |
| 2015/0354635 | A1 * | 12/2015 | Mcclymont | A61B 17/1631 408/126 |
| 2016/0228189 | A1 | 8/2016 | Goldenberg et al. | |
| 2017/0007272 | A1 | 1/2017 | Weitzman et al. | |
| 2021/0259803 | A1 * | 8/2021 | Patel | A61B 17/7082 |
| 2022/0096099 | A1 * | 3/2022 | Bhatia | A61B 17/1631 |
| 2022/0096110 | A1 * | 3/2022 | Bhatia | A61B 17/32002 |
| 2023/0080207 | A1 * | 3/2023 | Gunther | A61B 17/86 623/19.11 |
| 2023/0190308 | A1 * | 6/2023 | Bhatia | A61B 17/1624 606/79 |
| 2025/0169829 | A1 * | 5/2025 | McDowell | A61B 17/00234 |
| 2025/0221719 | A1 * | 7/2025 | Paproski | A61B 17/1631 |

FOREIGN PATENT DOCUMENTS

| | | | | |
|---|---|---|---|---|
| CN | 114828759 | A * | 7/2022 | ........ A61B 17/1675 |
| JP | 2016-147057 | A | 8/2016 | |
| JP | 2025509885 | A * | 4/2025 | ........ A61B 17/1695 |
| KR | 10-2011-0044470 | A | 4/2011 | |
| KR | 10-1068462 | B1 | 9/2011 | |
| WO | WO-2007142830 | A2 * | 12/2007 | ........ A61B 17/1622 |
| WO | WO-2015179967 | A1 * | 12/2015 | ............ B23B 41/00 |
| WO | WO 2017/074466 | A1 | 5/2017 | |
| WO | WO-2023113827 | A1 * | 6/2023 | ........... A61B 17/162 |
| WO | WO-2023183067 | A1 * | 9/2023 | ........ A61B 17/1695 |
| WO | WO-2024073728 | A2 * | 4/2024 | ........ A61B 17/1775 |
| WO | WO-2024156054 | A1 * | 8/2024 | ........ A61B 17/1633 |

OTHER PUBLICATIONS

Elder et al., "A Comparative Analysis of a Novel Modified Endoscopic Suturectomy (MES) Technique to Treat Craniosynostosis," Poster, Presented at Pennsylvania Neurosurgical Society Annual Meeting, Hershey, Pennsylvania, Jul. 19, 2025, 1 page.
International Preliminary Report on Patentability in International Appln. No. PCT/US2023/010400, mailed on Oct. 3, 2024, 10 pages.
International Search Report and Written Opinion in International Appln. No. PCT/US2023/010400, mailed on Apr. 12, 2023, 11 pages.
McDowell et al., "Sagittal Suture Synostosis: Key Points for Surgeons and Management Principles (Diagnosis, Surgical Considerations and Timing)," Neurosurgical Aspects of Craniosynostosis, Springer Nature, Jan. 2025, Chapter 7, pp. 87-96.
Partial Supplementary Search Report in European Appln. No. 23775418.9, mailed on Jan. 29, 2026, 13 pages.
Extended European Search Report in European Appln. No. 23775418.9, dated Apr. 20, 2026, 11 pages.

* cited by examiner

PRIOR ART

Side view of operation

Embodiment with an
upper guard and a foot
plate/guard with bit connected
to upper guard

DRIVE SYSTEM

DETAIL B
SCALE 4 : 1

DETAIL B
SCALE 4 : 1

DETAIL B
SCALE 4 : 1

DETAIL B
SCALE 4 : 1

SURGICAL DRILL FOR CRANIOSYNOSTOSIS AND ENDOSCOPIC PROCEDURES

CROSS-REFERENCE TO RELATED APPLICATIONS

This application is a National Stage application under 35 U.S.C. § 371 of International Application No. PCT/US2023/010400, having an International Filing Date of Jan. 9, 2023, which claims benefit of U.S. Provisional Patent Application Ser. No. 63/321,910, filed Mar. 21, 2022, the disclosure of which is incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Craniosynostosis is a dysfunction specific to the membranous type of bone formation, a mechanism most associated with skull and other flat bone development. In general, craniosynostosis is a birth defect in which the bones in the skull of a baby join together too early. Spaces between a baby's skull bones are typically filled with flexible material and are called sutures. The sutures allow the skull to grow as the brain grows. In craniosynostosis, one or more of the sutures closes too early, which can limit or slow the unimpeded growth of a baby's brain, cause skull deformities, and/or cause intracranial hypertension resulting in sequalae such as neurocognitive impairment and vision loss.

Craniosynostosis is divided into types based upon which suture(s) join together too early. The sagittal suture, for example, extends along the top of the head, from the baby's soft spot in the vicinity of the front of the head to the back of the head. Sagittal synostosis (SS), caused by premature fusion of the sagittal suture, restricts skull growth along the midline between the fontanelles which results in relative overgrowth at other sutures, producing cranial deformity as a result of excess elongation of the skull relative to its width that is known as scaphocephaly.

Craniosynostosis treatment may include surgery. Often, such surgeries are performed during the first year of life. Such surgeries may be open remodeling surgeries in which the surgeon makes a large ear to ear incision in the infant's scalp or less invasive, endoscopic surgeries. In children between the ages of three to six months of age, certain surgeons have shown a preference in recent years to perform a minimally invasive/endoscopic strip craniectomy with either post-operative helmeting or spring placement in patients. The endoscopic procedure requires a significantly smaller incision and results in less tissue disruption, blood loss, and anesthesia time.

Unfortunately, the surgical instruments available to surgeons in performing endoscopic bone surgeries (for example, endoscopic surgeries in craniosynostosis such as sagittal synostosis) are not sufficiently well suited to the task due, in part, to the unique trajectory of observation relative to the bone that is to be removed. There is thus a need to develop improved surgical instruments and related technologies.

SUMMARY

In one aspect, a surgical drill system for use with a drill bit includes a base and a drill head positioned forward of the base which is operatively connected to the base. The drill head includes a drill bit interface to which a shaft of the drill bit is attachable so that an axis of the shaft of the drill bit extends at an angle to (or relative to) an orientation of the drill head (that is, a forward-extending orientation or axis of the drill head) at the position of the drill bit interface. The surgical drill system further includes a drive system in operative connection with the drill bit interface which is configured to rotate the drill bit about the axis of the shaft of the drill bit when connected to the interface. In a number of embodiments, the drive system is a mechanical drive system or a pneumatic drive system.

In a number of embodiments, the drill head includes a support. The drill bit interface may, for example, be positioned on the support so that the shaft of the drill extends at the angle to the support at the position of the drill bit interface. The angle may, for example, be in the range of approximately 20° to approximately 100° to an axis of the support at the position of the drill bit interface. In a number of embodiments, the angle is in the range of approximately 30° to approximately 90° to the axis of the support at the position of the drill bit interface.

In a number of embodiments, the surgical drill system further includes a guard extending forward of the drill bit interface. The guard may, for example, be removably attached to the support or movably attached to the support. In a number of embodiments, the guard extends forward beyond a forwardmost portion of the drill bit.

In a number of embodiments, the drill head is rotatable relative to the base. In a number of embodiments, the drill head further includes a second member which extends forward and is spaced from the support. The second member may, for example, be positioned opposite the support and the drill bit is positioned between the support and the second member.

The surgical drill system in a number of embodiments includes an extending section which extends between the base and the drill head. The extending section may, for example, extend between the base and the drill head in a linear, curved, or curvilinear manner. In a number of embodiments, the extending section extends between the base and the drill head at an angle to the handle.

In another aspect, a method of performing endoscopic surgery includes endoscopically inserting a surgical drill system, wherein the surgical drill system includes a base and a drill head positioned forward of the base and being operatively connected to the base. The drill head includes a drill bit interface to which a shaft of a drill bit is attachable so that an axis of the shaft of the drill extends at an angle to (or relative to) an orientation of the drill head at the position of the drill bit interface. The surgical drill system further includes a drive system in operative connection with the drill bit interface which is configured to rotate the drill bit about the axis of the shaft of the drill bit when connected to the interface. In a number of embodiments, the drive system is a mechanical drive system or a pneumatic drive system.

As described above, in a number of embodiments, the drill head includes a support. The drill bit interface may, for example, be positioned on the support so that the shaft of the drill bit extends at the angle to the support at the position of the drill bit interface. The angle may, for example, be in the range of approximately 20° to approximately 100° to an axis of the support at the position of the drill bit interface, or in the range of approximately 30° to approximately 90° to the axis of the support at the position of the drill bit interface.

The surgical drill system further includes a guard extending forward of the drill bit interface in a number of embodiments. The guard may, for example, be removably attached to the support or movably attached to the support. In a number of embodiments, the guard extends forward beyond a forwardmost portion of the drill bit.

In a number of embodiments, the drill head is rotatable relative to the base. In a number of embodiments, the drill head further includes a second member which extends forward and is spaced from the support. The second member may, for example, be positioned opposite the support and the drill bit is positioned between the support and the second member.

The surgical drill system may, for example, include an extending section which extends between the base and the drill head. The extending section may, for example, extend between the base and the drill head in a linear, curved, or curvilinear manner. In a number of embodiments, the extending section extends between the base and the drill head at an angle to the base.

In another aspect, a method of performing endoscopic craniosynostosis surgery on a patient includes endoscopically inserting a surgical drill system. The surgical drill system includes a base and a drill head operatively connected to the base. A drill bit is rotatably attached to the drill head. The method further includes removing bone via the surgical drill system. In a number of embodiments, the method further includes placing a component between the bone and underlying soft tissue during removal of the bone to protect the underlying soft tissue from contact with the drill bit. The component may, for example, be a portion of an instrument, independent (or separate) from the drill system. The instrument may, for example, be a suction tube.

In a number of embodiments, the component is a component of the drill head. The drill head may, for example, further include a guard extending forward of the drill bit interface. In a number of embodiments, the guard is removably attached to the drill head. The guard may, for example, extend forward beyond a forwardmost portion of the drill bit.

In a number of embodiments, the drill head is rotatable relative to the base. In a number of embodiments, the drill head further includes a second member which extends forward and is spaced from the guard. The second member may, for example, be positioned opposite the guard and the drill bit is positioned intermediate between the guard and the second member.

In a further aspect, a surgical drill system for use with a drill bit includes a base and a drill head positioned forward of the base and being operatively connected to the base. The drill head includes a drill bit interface to which a shaft of the drill bit is attachable so that an axis of the shaft of the drill extends from the drill head at the position of the drill bit interface. The drill head further includes a guard extending forward of the drill bit interface. The surgical drill system further includes a drive system in operative connection with the drill bit interface which is configured to rotate the drill bit about the axis of the shaft of the drill bit when connected to the interface. The guard may, for example, be removably attached to the drill head. In a number of embodiments, the guard extends forward beyond a forwardmost portion of the drill bit. In a number of embodiments, the drill head is rotatable relative to the base.

The drill head may, for example, further include a second member which extends forward and is spaced from the guard. The second member may, for example, be positioned opposite the guard and the drill bit is positioned intermediate between the guard and the second member.

In a number of embodiments, an axis of the shaft of the drill extends at an angle to a forward extending orientation of the drill head at the position of the drill bit interface.

The present devices, systems, and methods, along with the attributes and attendant advantages thereof, will best be appreciated and understood in view of the following detailed description taken in conjunction with the accompanying drawings (which are not necessarily drawn to scale).

DETAILED DESCRIPTION

Figure 1A:
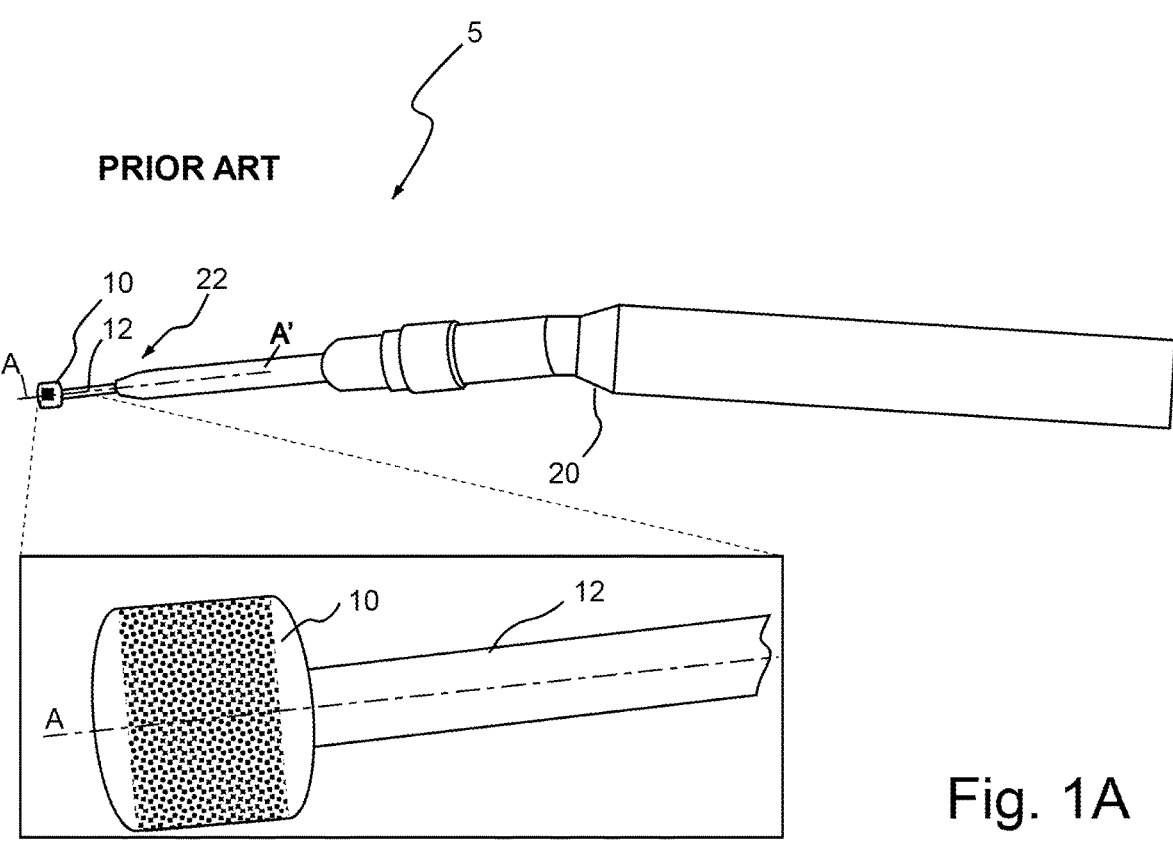
FIG. 1A illustrates an embodiment of a surgical drill commonly used in, for example, endonasal surgery with an enlarged view of the drill bit in an inset.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a guard" includes a plurality of such guards and equivalents thereof known to those skilled in the art, and so forth, and reference to "the guard" is a reference to one or more such guards and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

The terms "electronic circuitry", "circuitry" or "circuit," as used herein include, but is not limited to, hardware, firmware, software, or combinations of each to perform a function(s) or an action(s). For example, based on a desired feature or need, a circuit may include a software-controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software, or combinations of each to perform a function(s) or an action(s), or to cause a function or action from another component. For example, based on a desired application or need, logic may include a software-controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random-access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "controller," as used herein includes, but is not limited to, any circuit or device that coordinates and controls the operation of one or more input and/or output devices. A controller may, for example, include a device having one or more processors, microprocessors, or central processing units capable of being programmed to perform functions. In general, the term "input/output (IO) device" refers to any hardware used by a human operator/user or other systems to communicate with a processor/computer. Input/output devices are capable of sending data (output) to a computer and/or receiving data from a computer (input). User interface input/output devices include, for example, joysticks, mouses, keyboards, displays/touchscreen displays, cameras, voice recognition systems, motion control systems, etc.

The term "software," as used herein includes, but is not limited to, one or more computer readable or executable instructions that cause a computer or other electronic device to perform functions, actions, or behave in a desired manner. The instructions may be embodied in various forms such as routines, algorithms, modules, or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

In a representative endoscopic surgery for treatment/correction of sagittal synostosis, the patient is placed prone, supine, or lateral with the head secured in a horseshoe and generous local anesthetic with epinephrine is injected into the scalp after being scrubbed with a chlorhexidine brush. The head of the bed is typically rotated 180° away from the anesthesia team. The scalp is then generously sterilized with betadine solution after the incision is marked out. A 2-3 cm incision may, for example, be made just dependent to the midpoint between fontanelles to allow for the majority of endoscopic work to be done in a single direction. Other providers choose to use different techniques such as two separate 1 cm incisions on the skin overlying the front and back of the synostosis. The scalp is incised down to galea sharply and both edges are then elevated with skin hooks. Spot hemostasis is performed as needed and the pericranium is separated bluntly from the galea along the intended craniectomy pathway. Two lines are made off the midline bilaterally with a needle electrocautery, marking out typically a 1 cm boney strip to be removed. A burr hole is drilled at the posterior edge of the incision and off the cranial midline to avoid directly drilling on the sagittal sinus. The dura is dissected off of the adjacent bone with, for example, a modified Penfield 4 dissector. A rongeur may be used to extend the burr hole along the demarcated bone anteriorly. The craniectomy may be performed first in the dependent direction to prevent additional pooling of blood in the operative field from boney edges from higher points of the craniectomy. Skin hooks can be used to shift the scalp forward to allow for a greater length of removal with sequential dural dissection. The dependent suturectomy may be best extended to the fontanelle predominantly with rongeurs via scalp retraction with skin hooks or a lighted retractor if the incision is preferentially placed closer to one end of the synostosis than the other, as described above, or if there is an absence of easy video viewscreen visibility when the provider turns their body in the direction most suitable to operating in the dependent direction. The use of endoscopy in the reverse direction can be disorienting except if the surgical team is repositioned to face away from the patient's torso and towards the dependent fontanelle. Positioning the incision in this way avoids the inconvenience, risk of operative site contamination, and time expense of such a maneuver by necessitating a relatively small amount of bone removal in the dependent direction.

The lighted endoscope may be inserted by a co-surgeon and additional bites with a small eye rongeur may be taken after extending the dural dissection. It the experience of the present inventor, use of sinus instrumentation greatly reduces the time cost and difficulty of distal suturectomy. Once the comfortable reach of the rongeur has been exceeded, a straight Blakesley Thru-Cut forceps (Karl Storz, Germany) may, for example, be used to take additional midline bites. Curved Blakesely Ethmoid forceps (Karl Storz, Germany) or Pituitary Rongeurs (of various types as known to those skilled in the art) can be used to add additional lateral width to the suturectomy distally if the Thru-Cut is obstructed or otherwise insufficient. The dura is sequentially dissected as the suturectomy is further extended.

It is beneficial to withdraw the endoscope back intermittently to better visualize the course being taken. In that regard, surgeons often veer off over time away from the side of their dominant hand without intermittent correction. The sagittal sinus can serve as a good guide to midline as well but can become increasingly difficult to visualize during the distal portions of endoscopic work as a result of the increasingly parallel view of the endoscope relative to the dura. Paradoxically, the further from the incision one advances, the more advantageous and ergonomic drilling becomes due to the elongated, curved shaft of the drill.

In some cases, the parietal bones are insufficiently mobilized despite extending the suturectomy from fontanelle to fontanelle. In such cases, the proximal lambdoid sutures may be dissected off of the dura and additional suturectomy performed until the mobility is satisfactory. Depending on the operative plan, distractor springs may be inserted at this point of the procedure. It is important if springs are to be applied that the thickness of the bone along the suturectomy be examined. Particularly with young patients, the bone may be insufficiently resistant to allow for spring insertion and the operative plan may require revision. The dura should also be inspected to insure a sufficiently wide dissection off of the bone to prevent inadvertent dural injury with insertion of the spring footplates. The scalp may be closed in a standard fashion with absorbable sutures.

The bone thickness may be difficult to address with a number of sinus instruments. By using the endoscope to retract the scalp and a suction tip to retract the dura, the bone can be drilled down to the inner cortex safely under irrigation using, for example, a surgical drill or drill system 5 including, for example, a 4 mm coarse diamond round drill bit 10 as illustrated in FIG. 1A. A shaft 12 of drill bit 10 rotates about an axis A which is colinear or coaxial with the axis A' of a distal end or drill head 22 of drill system 5. In that regard, shaft 12 extends from distal end of drill head 22 parallel to or colinear with the orientation of axis of drill head 22, and drill bit 10 extends forward of any other component or portion of drill system 5. As used herein, the term "drill head" is that portion (typically an end section) of a drill or drill system that includes an interface to connect/removably connect a drill bit to the drive system of the drill. A short, angled drill handle 20 (such as available from Stryker of Kalamazoo, Michigan) may be more ergonomic than a straight handle and allow for more distal access. Such drills are, for example, used in endonasal surgery. A drilling technique is also helpful in addressing bone bleeding, as coarse diamond drill bit 10 provides a cauterizing effect. Young infants have a limited blood volume and it is desirable to limit bleeding. Depending on the angle, drill system 5 and/or a Thru-Cut forceps can be used to complete the inner cortex craniectomy efficiently until the fontanelle is reached. The parietal bones may be palpated through the scalp while being visualized with the endoscope to confirm appropriate mobility.

Figure 1B:
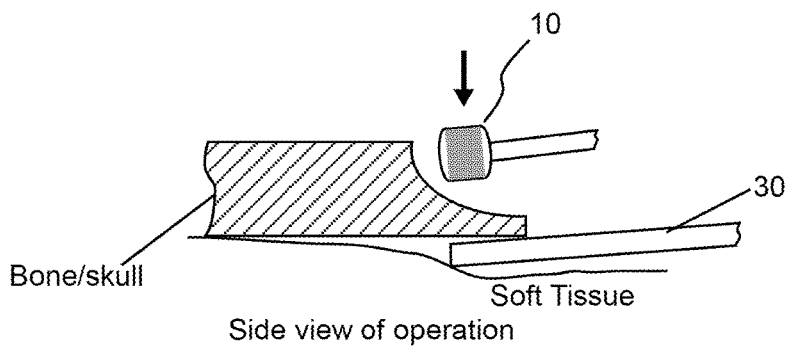
FIG. 1B illustrates schematically a surgical technique used by the inventor in performing craniosynostosis surgery using the surgical drill of FIG. 1A.

FIG. 1B illustrates schematically the use of drill bit 10 of drill system 5 in an embodiment of an endoscopic craniosynostosis surgery hereof. During the surgery, drill bit 10 must come downward into the bone from above toward the soft tissues underlying the skull as illustrated in FIG. 1B. Although the axial tips or ends of drill bit 10 are relatively smooth, the diamond-covered circumferential surface of the central or peripheral portion of drill bit 10 can cause significant damage to soft tissue underlying the skull. As illustrated in FIG. 1B, an instrument 30, which is independent or separate from drill system 5, such as a suction tube, can be used beneath the lower surface of the skull to protect from drill bit 10 contacting underlying soft tissue. In that regard, the soft tissue below the skull may be dissected to place, for example, a suction tube or other protective instrument including but not limited to a retractor or dissector underneath the skull to protect soft tissue from drill bit 10 (for example, the dura and the sagittal sinus).

Although drill systems such as drill system 5 has been applied to craniosynostosis by the present inventor with some significant success, drill system 5 has been found by the present inventor to be ergonomically inefficient in such an application. For example, use of drill system 5 necessitated development of a surgical technique hereof including the use of second instrument 30, separate or independent of drill system 5, such as a suction tube illustrated in FIG. 1B to protect intracranial soft tissues (dura, brain, blood vessels) from abrasion. Further, an additional instrument such as a Penfield 4 dissector is required to separate the bone from the dura prior to advancing a retracting device between the bone and the dura.

In a number of embodiments of drill heads of drill systems hereof, a drill bit is attachable to a drill bit interface (typically removably attachable) so that the shaft of the drill extends at an angle to a forward extending orientation of the drill head (as determined at the position of the drill bit interface). A component or section of the drill head may, for example, extend forward and along an orientation or axis different from the axis of the drill bit shaft at the position of an interface to which the drill bit shaft is attachable. Such a component or section may, for example, function to protect soft tissue in the vicinity of the drill bit (for example, below the drill bit in the case of craniosynostosis surgery) or to assist in dissecting the dura from the bone prior to drilling. Further, the shaft of the drill bit may extend from the drill bit interface of the drill head at an angle to facilitate advancement of a sharp cutting portion of drill bit into bone en face during bone removal.

Figure 2:
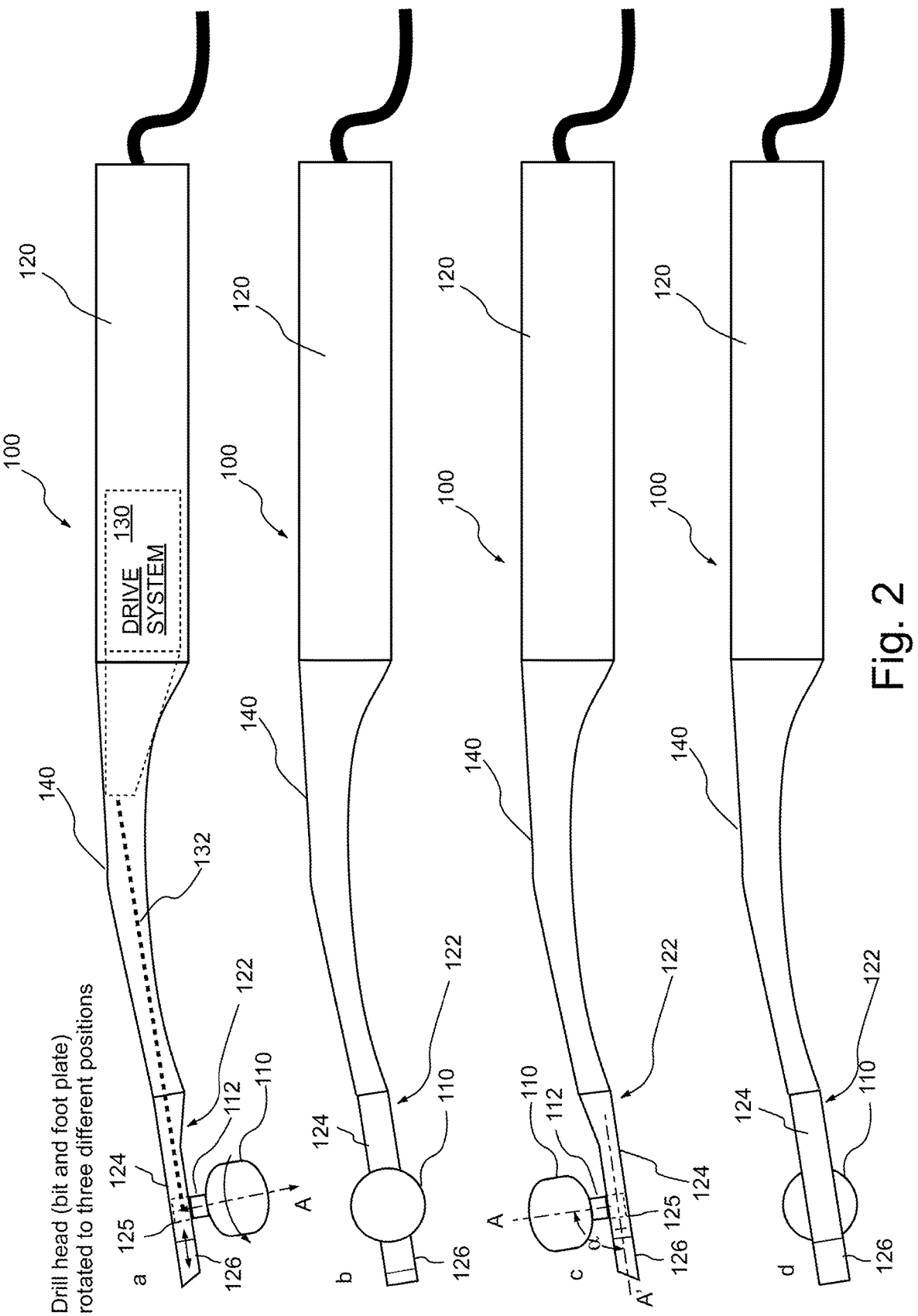
FIG. 2 illustrates an embodiment of a surgical drill, surgical drill instrument or surgical drill system hereof in which a distal end or drill head of the drill system to which the rotating drill bit is attached is rotated about its axis to four different positions separated by approximately 90 degrees of rotation, and wherein the drill bit rotates about an axis A which extends at an angle α to (for example, generally perpendicular to) to the orientation or axis of extension of the distal end of the drill.

In that regard, FIG. 2 illustrates an embodiment of a drill system 100 hereof. Unlike drill system 5, in which drill bit 10 rotates about an axis which is aligned, collinear, coaxial or parallel with an orientation/axis of a distal end of drill head 22 of drill 5, drill bit 110 rotates about an axis A (of a shaft 112 thereof) which is oriented at an angle α (for example, in the range of approximately 20° to approximately 110°, or within the range of approximately 30° to approximately) 90° to the (forward-extending) orientation (for example, of an axis A') of a drill head 122 of drill system 100 at the position of a drill bit interface 125. In the embodiment illustrated in FIG. 2, axis A is oriented approximately perpendicularly or at approximately 90° to the orientation of a drill head 122 of drill system 100 at the position of a drill bit interface 125. As used herein with respect to a given angle α, the term "approximately", refers to an orientation which is within 10% or within 5% of the degree of the angle described.

In a number of embodiments, drill head 122 may be rotatable about its axis so that the orientation or the axis of drill bit 110 relative to a base or handle 120 of drill system 100 is adjustable. In the embodiment illustrated in FIG. 2, drill head 122 is rotatable relative to an extending section 140 (which extends between base or handle 120 and drill head 122) to four positions as illustrated in panels a through d. Drill bit 110 illustrated in FIG. 2 is a representative example of a suitable drill bit for use in connection with drill system 100 and other drill systems hereof. Many types of drill bits as, for example, known in the medical arts may be used in connection with the drill systems hereof.

In the embodiment of FIG. 2, drill head 122 includes a forward extending support 124 including drill bit interface 125 to which a shaft 112 of drill bit 110 is removably attachable and from which shaft 112 extends upon attachment. A drive system 130 (see panel a of FIG. 2), which may, for example, include an electric or a pneumatic motor, is operatively connected to shaft 112 to rotate drill bit 110 by a connective mechanism 132 (see panel a of FIG. 2) including, for example, a rotating shaft, a chain system, or a belt system. Non-parallel shafts such as drill bit shaft 112 and a rotating shaft of connective mechanism 132 may, for example, be operatively connected via bevel gears as known in the mechanical arts in a number of embodiments. Drive system 130 may also be a pneumatic drive system. Axis A of drill bit shaft 112 may or may not extend at an angle with respect to the orientation or axial orientation of base or handle 120) (depending, for example, on the relative orientation of drill head 122 to base or handle 120). However, the extension of drill bit shaft 112 at angle α relative to the orientation of drill head 122 at the position of a drill bit interface 125 facilitates the manipulation of base or handle 120 to approach bone at various angles while providing protection for surrounding soft tissue.

As used herein to describe drill system 100, the terms "axial" or "axially" (or similar terms) refer generally to one or more axes around which a portion or component of system 100 (for example, drill bit 110, drill head 122, support 124, base or handle 120) is formed (although not necessarily symmetrically therearound). Such an axis can be a linear axis, curvilinear axis, or a curved axis. The terms "proximal" or "rearward" refer generally to a direction toward base or handle 120. The terms "distal" or "forward" refer generally to a direction toward a drill head 122/drill bit 110. The term "radial" refers generally to a direction normal to an axis.

Figures 3A, 3B:
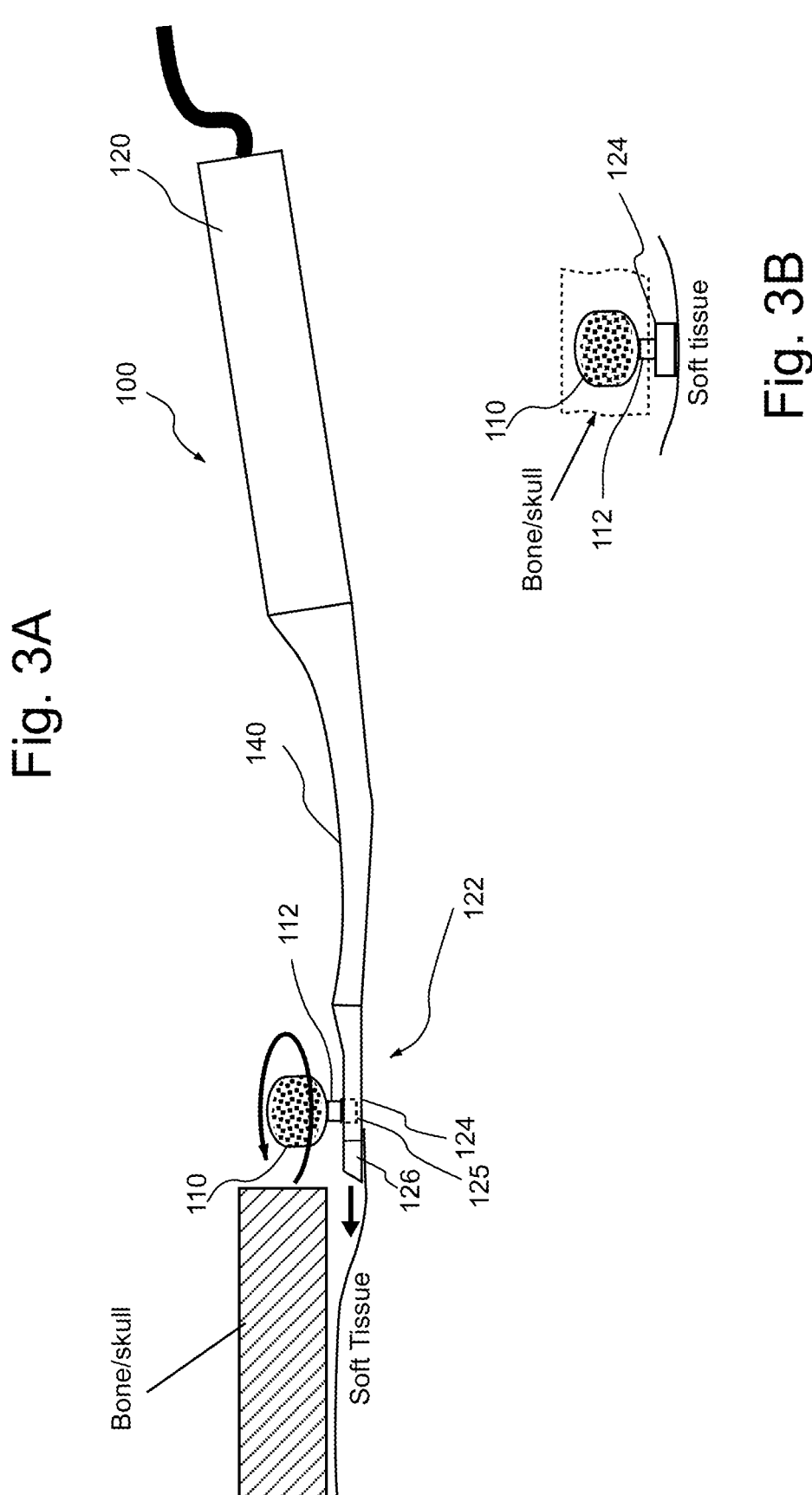
FIG. 3A illustrates a side, schematic view of craniosynostosis surgery hereof using the surgical drill instrument of FIG. 2.
FIG. 3B illustrates a front, schematic view of craniosynostosis surgery hereof using the surgical drill instrument of FIG. 2.

FIG. 3A illustrates a side, schematic view of an embodiment of craniosynostosis surgery using surgical drill instrument 100 of FIG. 2, while FIG. 3B illustrates a front, schematic view of such surgery. As illustrated in FIGS. 3A and 3B, the orientation of drill bit 110 allows advancement of drill bit 110 into the bone of the skull en face such that the sharp cutting portion of drill bit 110 are oriented generally in plane with the skull while the dull, axial ends of drill bit 110 may be oriented toward the soft tissue. Further, support 124 may operate as a guard to shield soft tissue below the skull from the cutting and may be used divert soft tissue away from drill bit 110. In a number of embodiments, support 124 is sufficiently wide to ensure that soft tissue is diverted or pushed aside and prevented from contacting drill bit 110. Support 124 may, for example, be at least one half as wide as the diameter of drill bit 110 or at least as wide as the diameter of drill bit 110. Support 124 may include a forward guard section or guard 126 which extends beyond the forward perimeter of drill bit 110. Forward guard 126 may, for example, be removable or telescopically extendible/retractable for facilitating various procedures. Various widths and/or lengths of support 124 and forward guard section or guard 126 may be produced to accommodate various sized drill bits.

The drill instruments 100 hereof function well in drilling/removing bone over various orientations in addition to or different from the orientation of the bone/skull illustrated in FIGS. 3A and 3B. Drill instruments 100 hereof function particularly well in situations when the bone is oriented perpendicular, parallel, or at other angles therebetween.

Figure 3C:
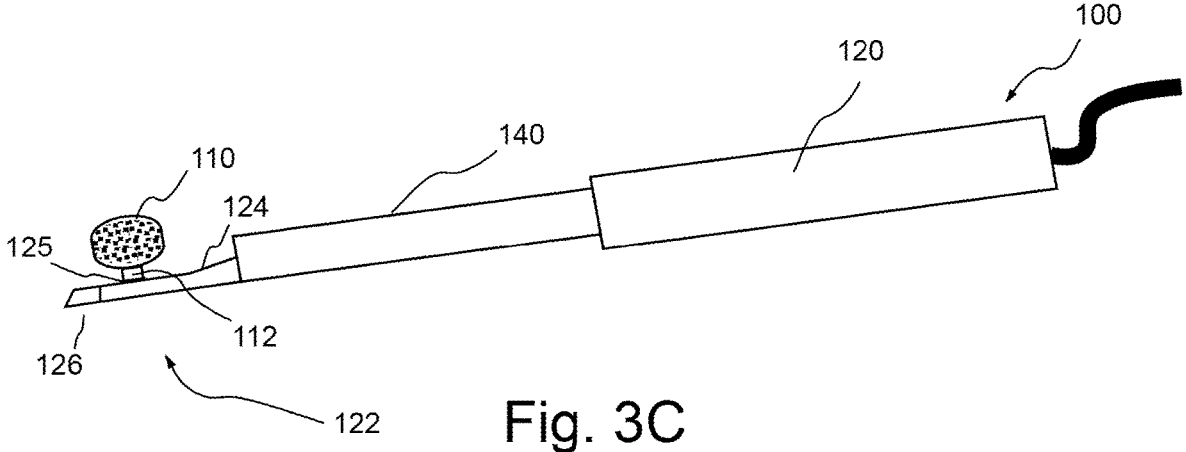
FIG. 3C illustrates a side, schematic view of another embodiment of a surgical drill instrument hereof with a generally linear extending section which extends between a base or handle and a drill head.

In the illustrated embodiment, extending section 140 of drill instrument 100 extends in an angled or curved path to facilitate orientation and extension of drill bit 110 in the plane of the skull. In the case of relatively thick bone structures, multiple forward or en face movements of surgical drill instrument or system 100 may occur to fully remove a section of bone. In other embodiments, extending section 140 may extend in a straight or linear manner from base or handle 120 as illustrated in FIG. 3C. Extending section 140 may also extend in a curvilinear manner or in an angled manner from base or handle 120. Extending sections of different lengths as well as straight, angled, curved, curvilinear, etc. extending sections may be interchangeable in a single drill system 100 for facilitating the use of drill system 100 in different procedure and/or by users.

Figure 4:
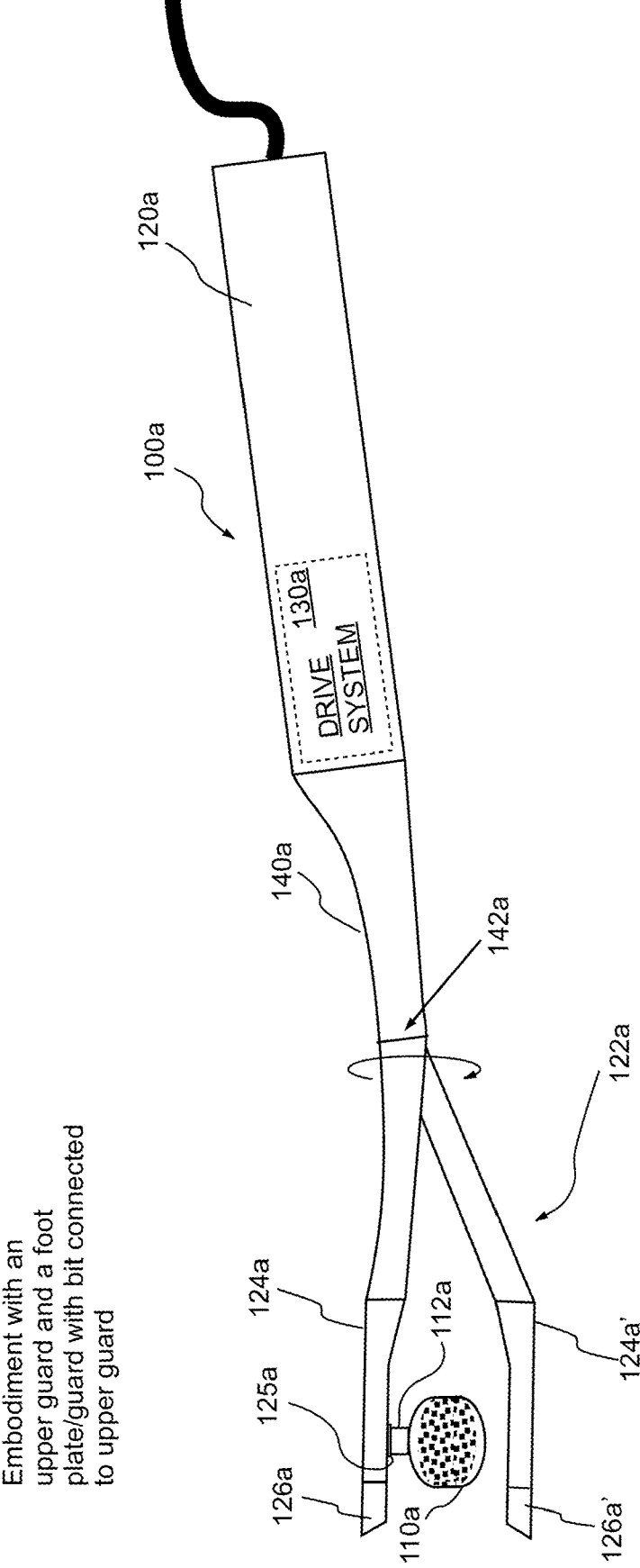
FIG. 4 illustrates another embodiment of a surgical drill hereof including an upper guard and a foot or lower guard.
Figures 5A, 5B:
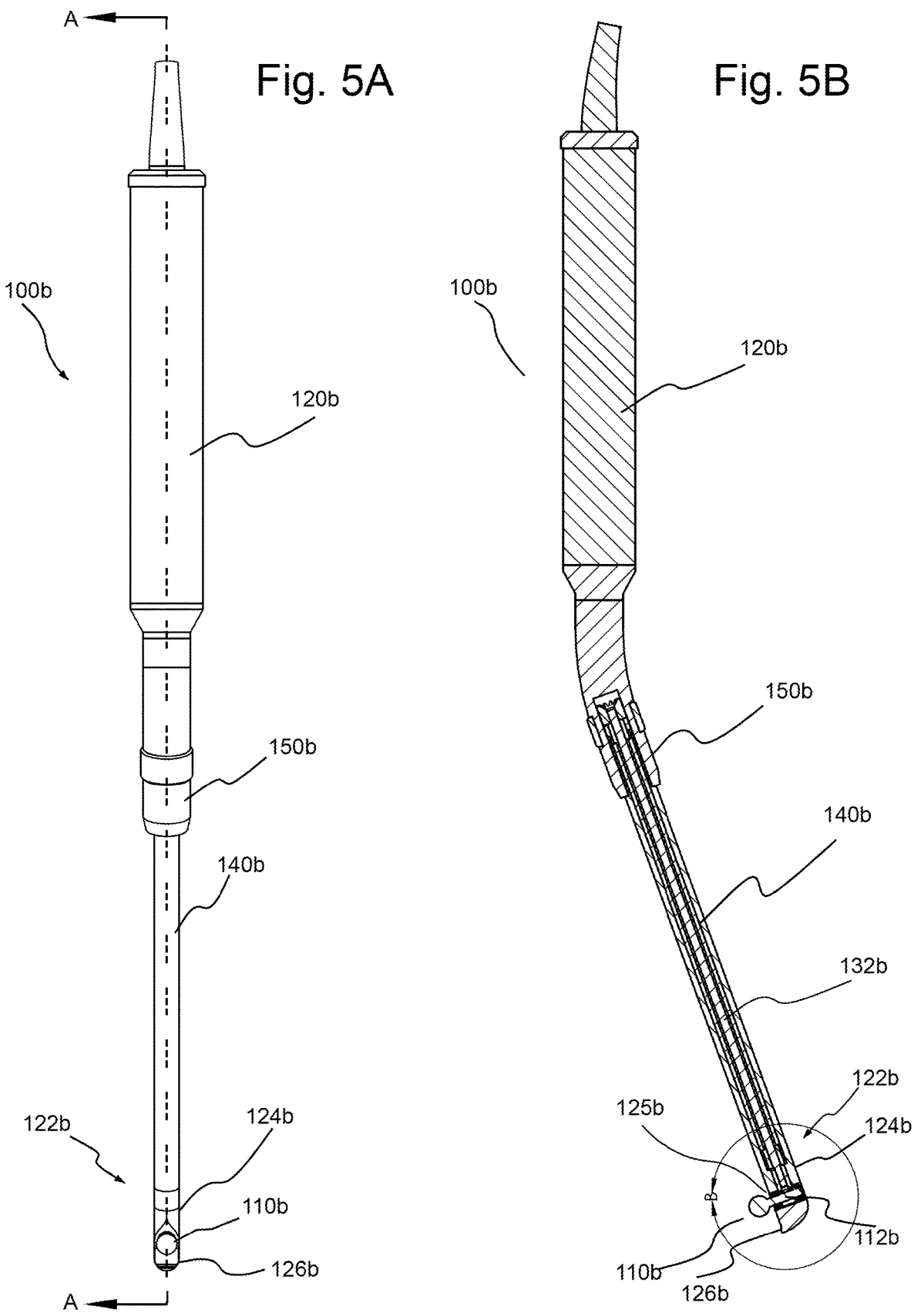
FIG. 5A illustrates a top plan view of another embodiment of a surgical drill, instrument or surgical drill system hereof in which the rotating drill bit is mechanically driven.
FIG. 5B illustrates a side, cross-sectional view of the surgical drill of FIG. 5A along section A-A of FIG. 5A.
Figures 5C, 5D:
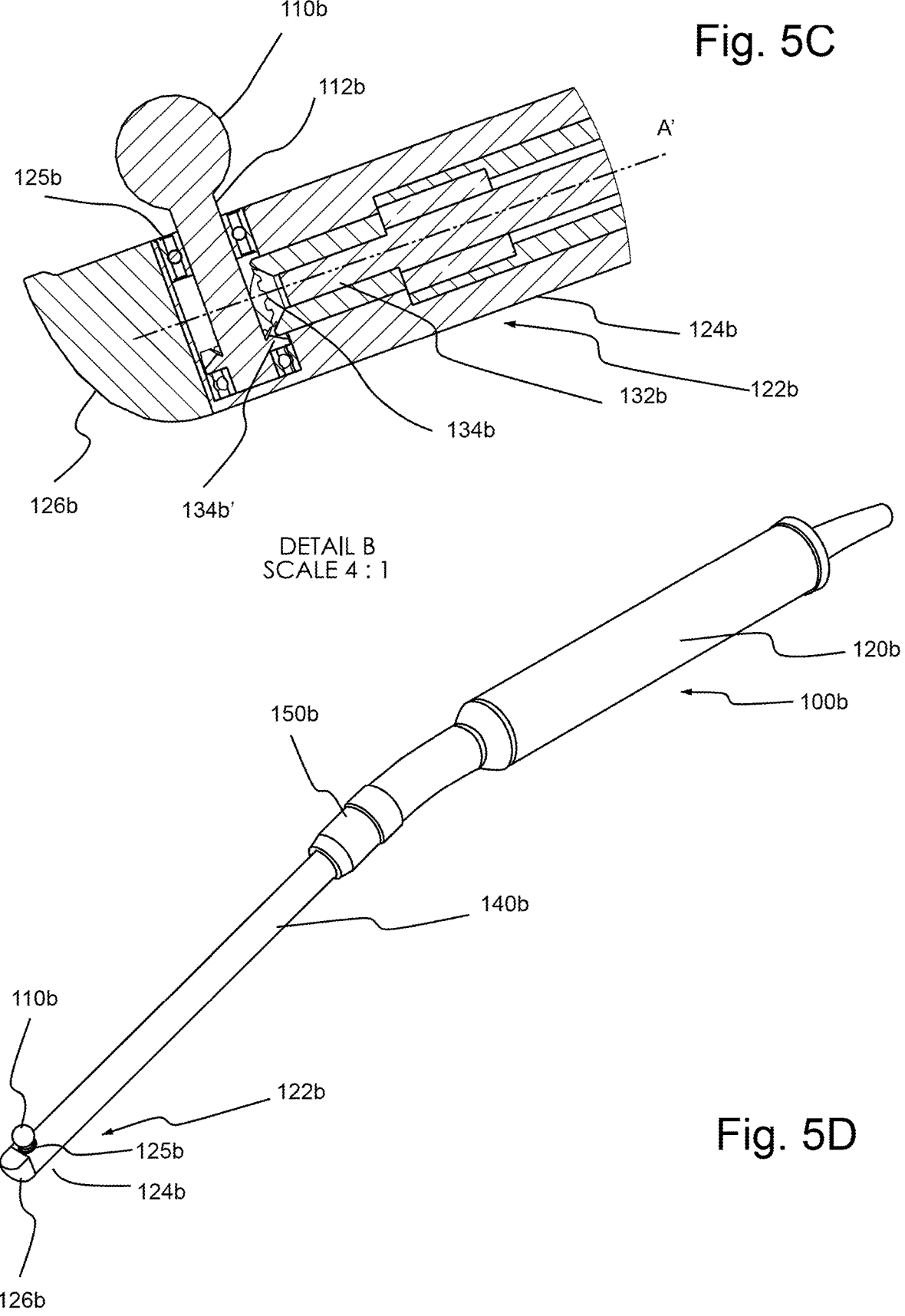
FIG. 5C illustrates an enlarged portion of the surgical drill of FIG. 5A in the vicinity of the drill head as indicated by encircled section B of FIG. 5B and illustrates the drill bit-interface extending at an angle to the orientation of the drill head and the support thereof.
FIG. 5D illustrates an isometric view of the surgical drill of FIG. 5A.
Figures 6A, 6B:
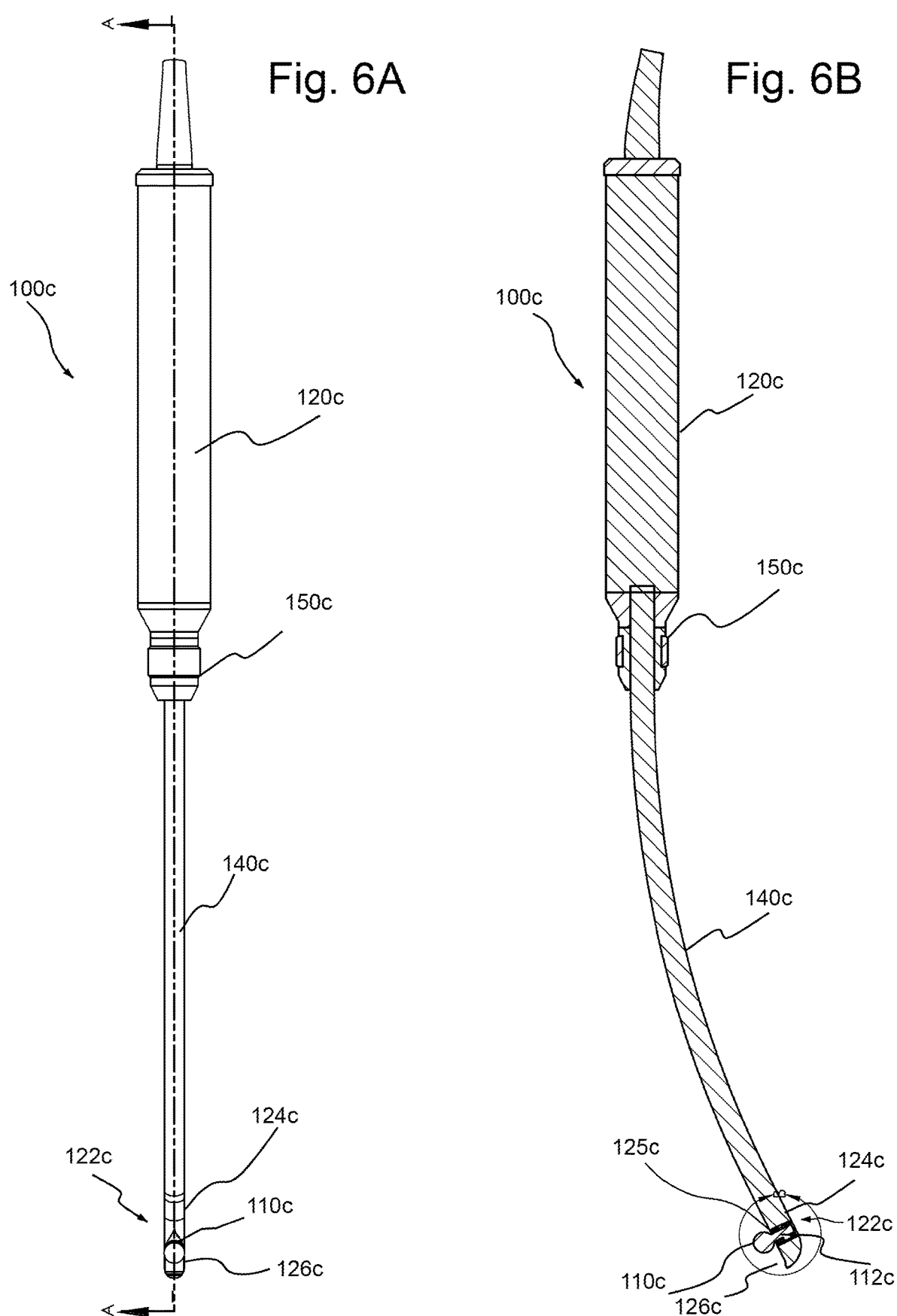
FIG. 6A illustrates a top plan view of another embodiment of a surgical drill, instrument or surgical drill system hereof, similar in function to the embodiment of FIG. 5A, in which the rotating drill bit is pneumatically driven.
FIG. 6B illustrates a side, cross-sectional view of the surgical drill of FIG. 6A along section A-A of FIG. 6A.
Figures 6C, 6D:
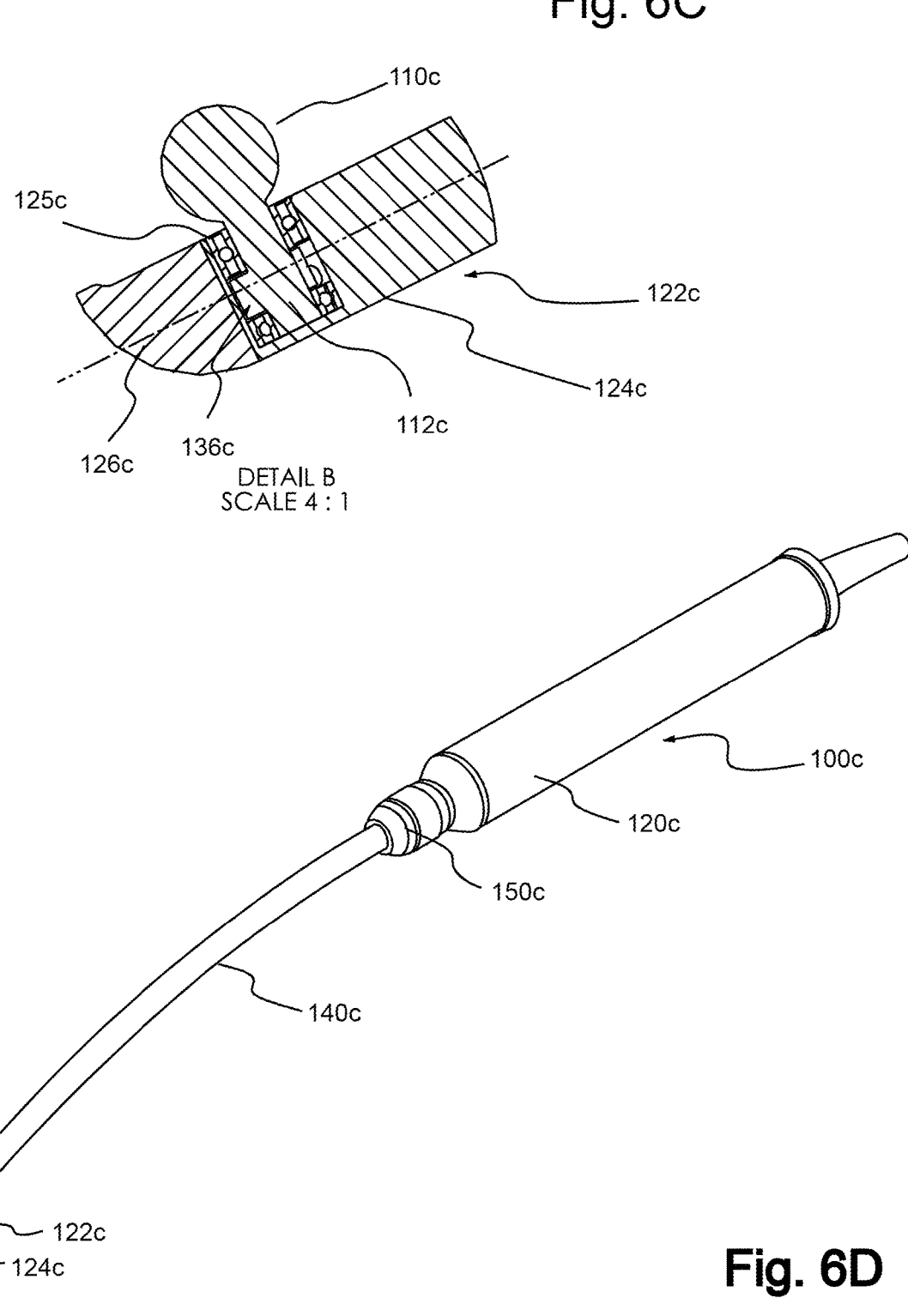
FIG. 6C illustrates an enlarged portion of the surgical drill of FIG. 6A indicated by encircled section B of FIG. 6B.
FIG. 6D illustrates an isometric view of the surgical drill of FIG. 6A.
Figures 7A, 7B:
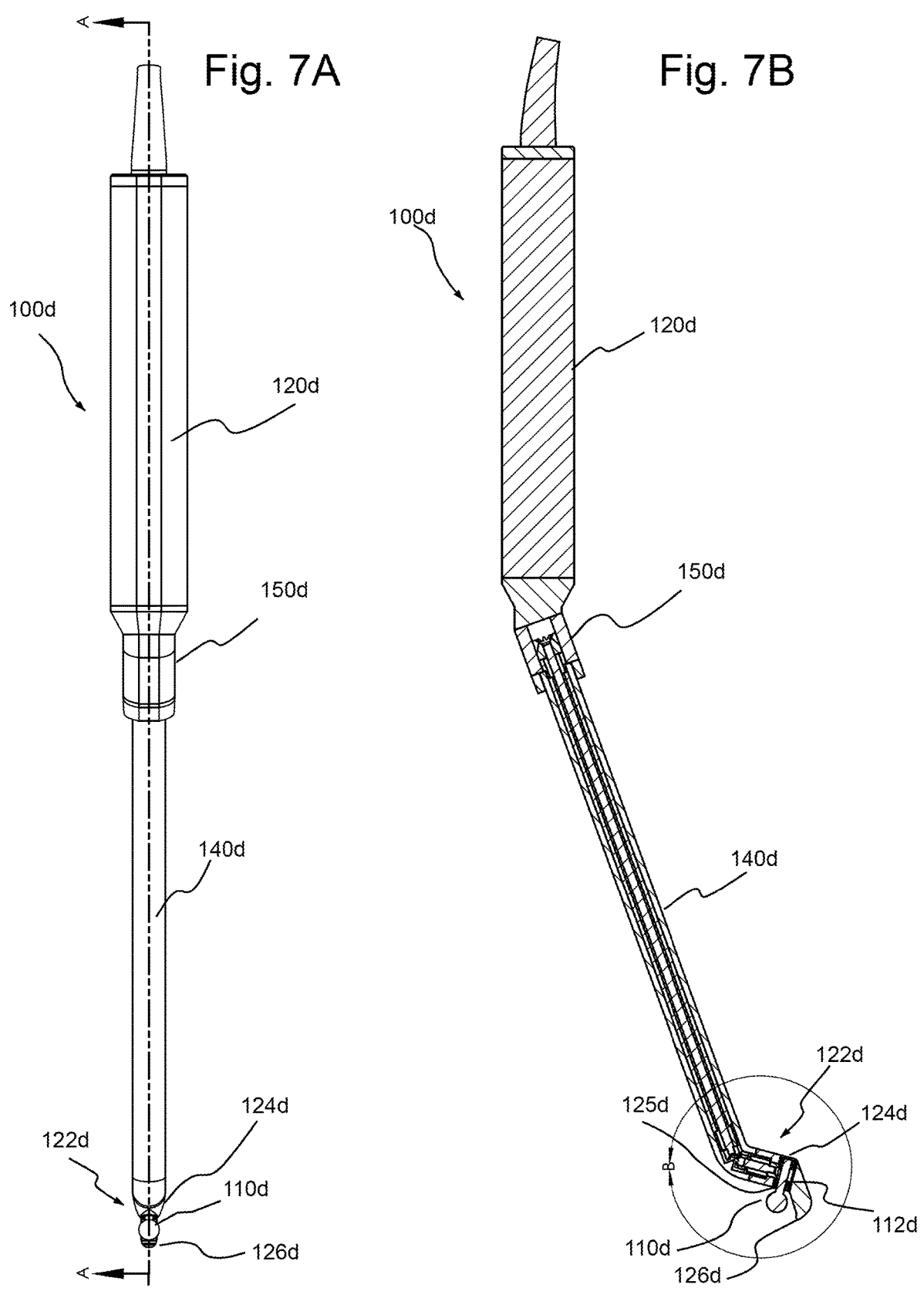
FIG. 7A illustrates a top plan view of another embodiment of a surgical drill, instrument or surgical drill system hereof in which the rotating drill bit is mechanically driven.
FIG. 7B illustrates a side, cross-sectional view of the surgical drill of FIG. 7A along section A-A of FIG. 7A.
Figures 7C, 7D:
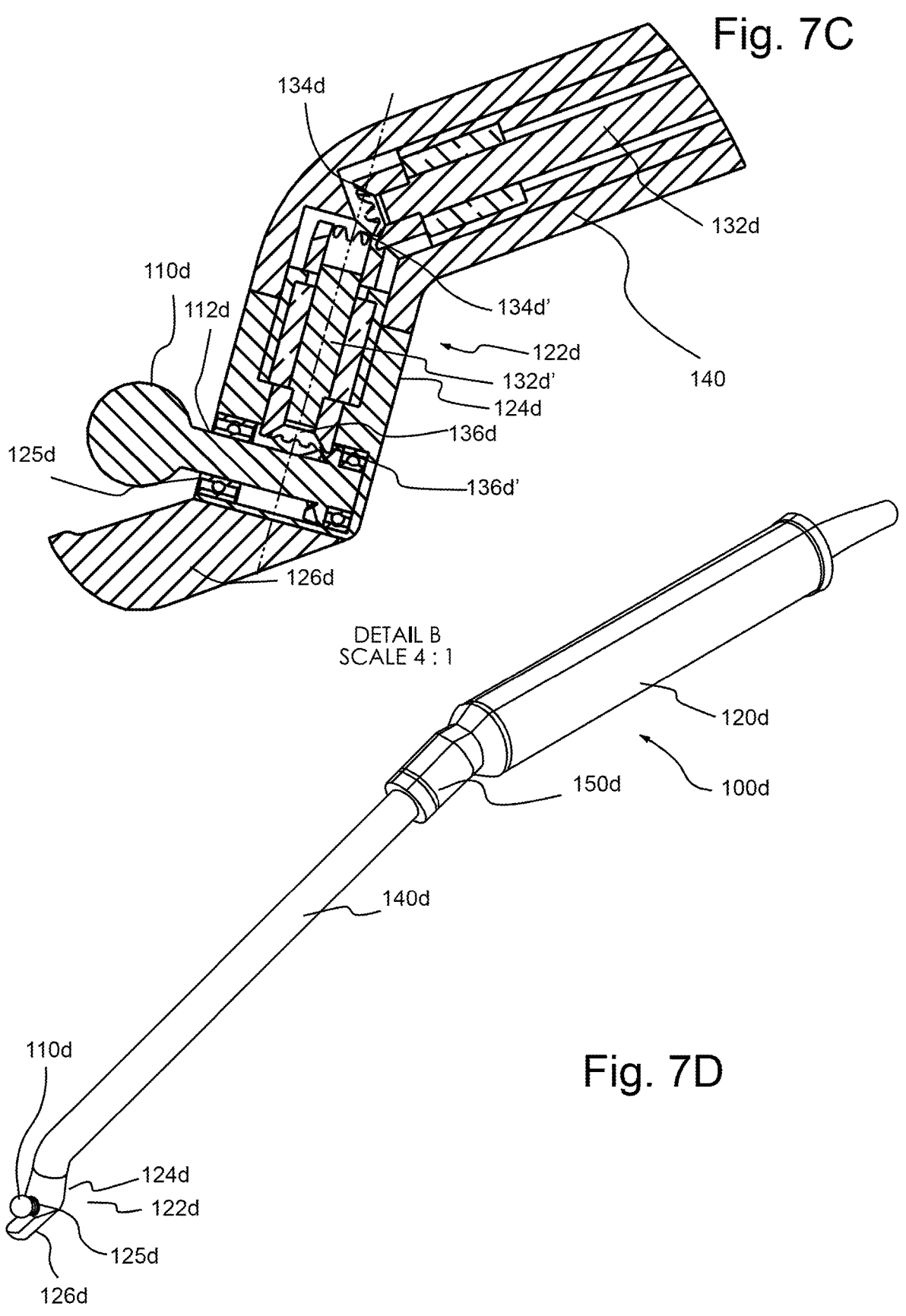
FIG. 7C illustrates an enlarged portion of the surgical drill of FIG. 7A indicated by encircled section B of FIG. 7B.
FIG. 7D illustrates an isometric view of the surgical drill of FIG. 7A.

FIG. 4 illustrates another embodiment of a surgical drill, surgical drill system or instrument 100*a* hereof. In many respects, drill system 100*a* is constructed similarly to drill system 100 and components of drill system 100*a* are numbered similarly to like components of drill system 100 with addition of the designation "a" to the reference number. In drill system 100*a*, drill head 122*a* includes an extending support or support 124*a* (from which drill bit shaft 112*a* extends via an interface 125*a*) and at least a second extending member 124*a'* spaced from (for example, positioned generally opposite of or rotated approximately 180° from) and oriented generally parallel to (that is, within 10% or with 5% of parallel, or parallel) support 124*a*. Support 124*a* and second, extending member 124*a'* may include forward guards 126*a* and 126*a'*, which operate similar to forward guard 126 of drill system 100. Drill head 122*a* may, for example, be rotatable relative to extension or extending section 140*a* at connection point 142*a* or elsewhere. As illustrated in FIGS. 2 and 4, support 124, 124*a*, to which drill bit 110, 110*a* is operatively connected, may be rotated to a number of positions so that drill bit 110, 110*a* rotates in various planes of rotation to facilitate a particular surgical task or drilling procedure in multiple directions/orientations. In the embodiment of FIG. 4, extending support 124*a* and second, extending member 124*a'*, respectively, may assist in protecting and diverting soft tissue positioned adjacent each axial end of drill bit 110*a* (which extends between extending support and second extending member 124*a* and 124*a'*, respectively). As discussed above for support 124 of drill system 100, one or both of guards 126*a* and 126*a'* may be extendable/retractable relative to support 124*a* and second extending member 124*a'*, respectively, as well as be removable from connection with drill system 100*a*.

As compared to drill 10 of FIGS. 1A and 1B, drills hereof reduce the likelihood of inadvertent contact of the drill bits hereof with surrounding/underlying soft tissues and allow for en face, parallel drilling of target bone. The one or more guards of the drills hereof enable simultaneous displacement of soft tissue above the bone (such as scalp tissue) and/or below the bone (such as intracranial tissue) or assist in the dissection of such soft tissues off of bone prior to displacement.

Because axis 112, 112*a* of drill bit 110, 110*a* may extend at an angle from (or not parallel to) a drive shaft of drive system 130, 130*a*, it may be desirable to use a mechanical gear connection designed to operatively connect non-parallel rotating shafts in a number of embodiments hereof. Such gear connections include, for example, spiral worm gears and bevel gears. Chain driven gears may be used in certain embodiments to connect a drive shaft drive system 130, 130*a* to shaft or axis 112, 112*a* of drill bit 110, 110*a*. One skilled in the mechanical art can readily design a system for drive and control of rotation of drill bits hereof on the basis of surgical requirements and engineering principles. In other embodiments, pneumatic power may be used to drive axis 112, 112*a* of drill bit 110, 110*a*.

FIGS. 5A through 5D illustrate another embodiment of a surgical drill instrument or surgical drill system 100*b* hereof in which the rotating drill bit is mechanically driven. In many respects, drill system 100*b* is constructed similarly to drill system 100 and components of drill system 100*a* are numbered similarly to like components of drill system 100 with addition of the designation "b" to the reference number. In the embodiment of FIGS. 5A through 5D, extending section 140*b* extends in a generally linear direction from a connector 150*b* in operative connection with base or handle 120*b*. Connector 150*b* is oriented at an angle to base or handle 120*b*. Support 124*b* of drill head 122*b* extends along the same orientation as extending section 140*b* and may simple be considered a distal end section thereof. In the embodiment of drill system 100*b*, shaft 112*b* of drill bit 110*b* extends perpendicular or orthogonal to the orientation of support 124*b* at the point of interface 125*b*. As, for example, illustrated in FIG. 5C, the mechanical drive system may include a drive shaft 132*b* (which may be flexible) which is in operative connection with a gear system including a first gear 134*b* which rotates around the axis of drive shaft 132*b*. A second gear 134*b'* is driven by first gear 134*b* and rotates about an axis (colinear with the axis of drill bit shaft 112*b*) which is orthogonal to the axis of drive shaft 132*b* and first gear 134*b*.

FIGS. 6A through 6D illustrate another embodiment of a surgical drill instrument or surgical drill system 100*c* hereof in which the rotating drill bit is pneumatically driven. In many respects, drill system 100*c* is constructed similarly to drill system 100*b* and components of drill system 100*c* are numbered similarly to like components of drill system 100*b* with substitution of the designation "c" in the reference number. In the embodiment of FIGS. 6A through 6D, extending section 140*c* extends in a in a curved or curvilinear orientation from a connector 150*c* in operative connection with base or handle 120*c*. Connector 150*c* is oriented in a colinear or coaxial direction relative to base or handle 120*c*. Extending section 140*c* extends from connector 150*c* in a curved manner. Support 124*b* of drill head 122*b* extends in a generally linear or curvilinear direction at a distal end of extending section 140*c*. In the embodiment of drill system 100*c*, shaft 112*c* of drill bit 110*c* extends perpendicular or orthogonal to the orientation of support 124*c* at the point of interface 125*c*. With respect to base or handle 120*c*, drill bit shaft 112*c* is positioned and oriented very similarly to the position of and orientation of drill bit shaft 112*b* relative to base or handle 120*b*. As, for example, illustrated in FIG. 6C, the pneumatic drive system may, for example, includes a pneumatically driven rotor 136*c* (for example, including rotor vanes) which is in operative connection with a source of pressurized gas/air to rotate drill bit 110*c* about the axis of shaft 112*c*.

FIGS. 7A through 7D illustrate another embodiment of a surgical drill instrument or surgical drill system 100*d* hereof in which the rotating drill bit is mechanically driven. In many respects, drill system 100*d* is constructed similarly to drill system 100*b* and components of drill system 100*d* are numbered similarly to like components of drill system 100 with the substitution of the designation "d" in the reference number. In the embodiment of FIGS. 7A through 7D, extending section 140*d* extends in a generally linear direction from a connector 150*d* in operative connection with base or handle 120*d*. Connector 150*d* is oriented at an angle to base or handle 120*d*.

Support 124*d* of drill head 122*d* extends at an angle relative to the orientation of extending section 140*d*. Shaft 112*d* of drill bit 110*d* extends generally perpendicular or orthogonal to the orientation of support 124*d* at the point of interface 125*d*. As, for example, illustrated in FIG. 7C, the mechanical drive system includes a flexible drive shaft 132*d* which is in operative connection with a first gear system including a first gear 134*d* which rotates around the axis of drive shaft 132*d*. A second gear 134*d'* is driven by first gear 134*d* and rotates about an axis which at an angle relative to first gear 134*d*. Second gear 134*d'* drives a second drive shaft 132*d'* which passes through support 124*d* and terminates in a third gear 136*d*. Third gear 136*d* drives a fourth gear 136*d'*, which rotate drill bit shaft 112*d* about its axis. Forward guard section or guard 126*d* extends at an angle to the orientation of support 124*d*.

FIGS. 8A through 8D illustrate another embodiment of a surgical drill instrument or surgical drill system 100*e* hereof in which the rotating drill bit is pneumatically driven. In many respects, drill system 100*e* is constructed similarly to drill system 100*c* and components of drill system 100*e* are numbered similarly to like components of drill system 100*c* with substitution of the designation "e" in the reference number. In the embodiment of FIGS. 8A through 8D, extending section 140*e* extends in a in a curved or curvilinear orientation from a connector 150*e* in operative connection with base or handle 120*e*. Connector 150*e* is oriented in a colinear or coaxial direction relative to base or handle 120*e*. Support 124*e* of drill head 122*e* extends in a generally linear or curvilinear direction at a distal end of extending section 140*e*. In the embodiment of drill system 100*e*, shaft 112*e* of drill bit 110*e* extends at an angle (but not perpendicular or orthogonal) to the orientation of support 124*e* at the point of interface 125*e*. With respect to base or handle 120*e*, drill bit shaft 112*e* is positioned and oriented very similarly to the position and orientation of drill bit shaft 112*d* relative to base or handle 120*d*. As, for example, illustrated in FIG. 8C, the pneumatic drive system may, for example, includes a pneumatically driven rotor 136*e* (for example, including rotor vanes) which is in operative connection with a source of pressurized gas/air to rotate drill bit 110*e* about the axis of shaft 112*e*. In general, as illustrated in a comparison of the embodiments of drill system 110*d* and 110*e*, use of a pneumatic drive may simplify the orientation of drill bits hereof in various angles relative to the support members and bases/handles hereof.

As sagittal synostosis surgery is the most common surgically corrected synostosis, the above surgical description focuses on sagittal synostosis as a representative example. However, the utility of drill systems hereof is equal or greater in less common synostosis as a result of the proximity of other sutures to the skull base, where the skull naturally thickens. For example, drill systems hereof may be particularly useful at the nasofrontal junction in metopic synostosis as well as in drilling the greater wing of the sphenoid bone in coronal synostosis. Moreover, drill system hereof may be used in surgeries other than craniosynostosis surgeries. For example, in the representative example of endonasal surgery, drill systems hereof may be used to rapidly drill the rostrum of the sphenoid bone. Representative examples of surgeries in which the drill systems hereof may be used include, but are not limited to, surgeries involving the sphenoid rostrum and planum sphenoidale, the pterygoid bone, the medial orbital wall, the maxilla, maxillary crest, and maxillary walls, the hard palate, the anterior fossa floor, the middle fossa floor, and the clivus/ventral components of the posterior fossa. Such surgeries may benefit from the ability to detach or extend/retract soft tissue guards such as guards 126, 126*a*, 126*a'*, 126*b*, 126*c*, 126*d*, and/or 126*e* hereof. In general, the drill systems hereof may be used in any procedure in which en face drilling of the target bone is desirable.

Figures 8A, 8B:
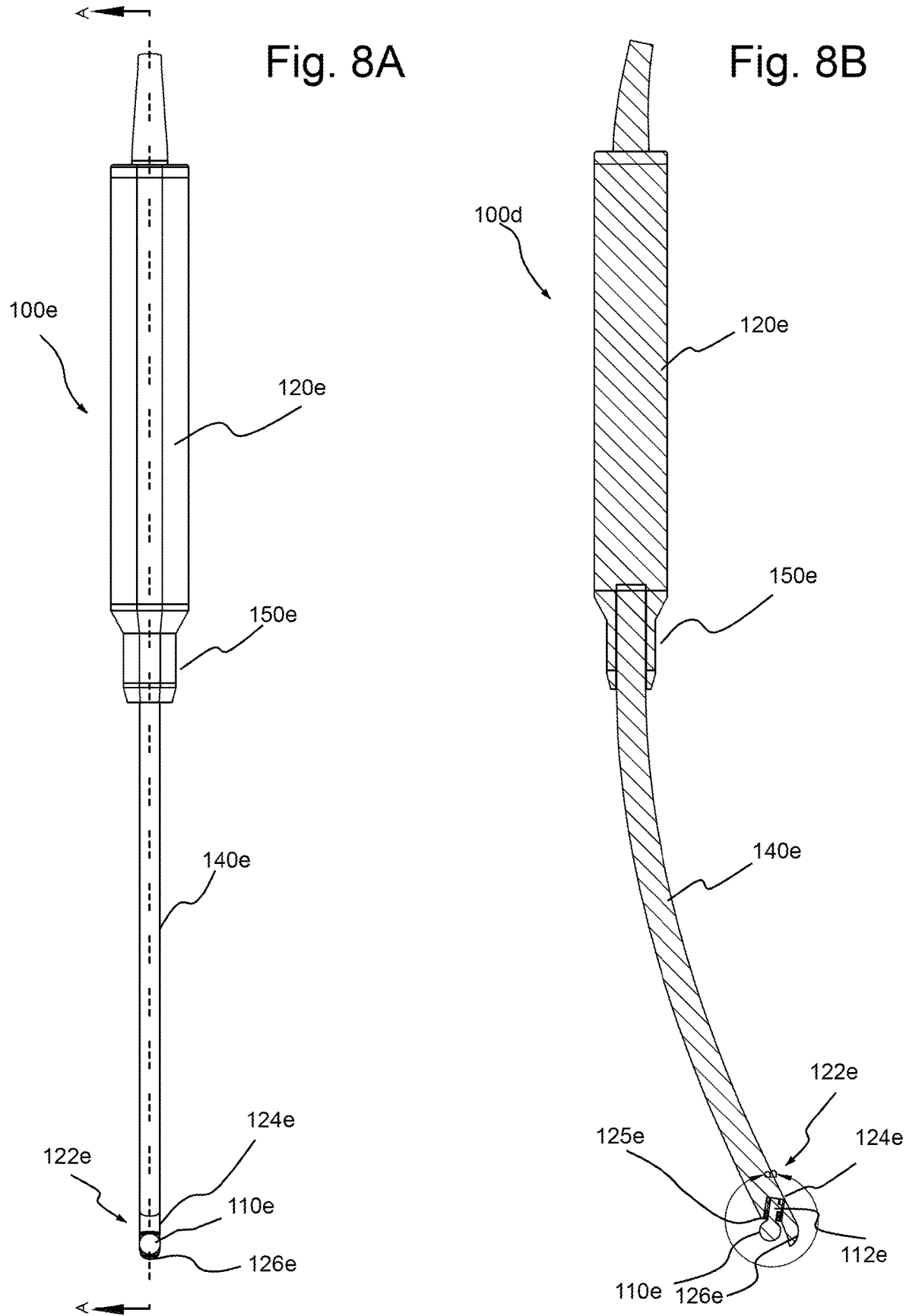
FIG. 8A illustrates a top plan view of another embodiment of a surgical drill, instrument or surgical drill system hereof, similar in function to the embodiment of FIG. 7A, in which the rotating drill bit is pneumatically driven.
FIG. 8B illustrates a side, cross-sectional view of the surgical drill of FIG. 8A along section A-A of FIG. 8A.
Figures 8C, 8D:
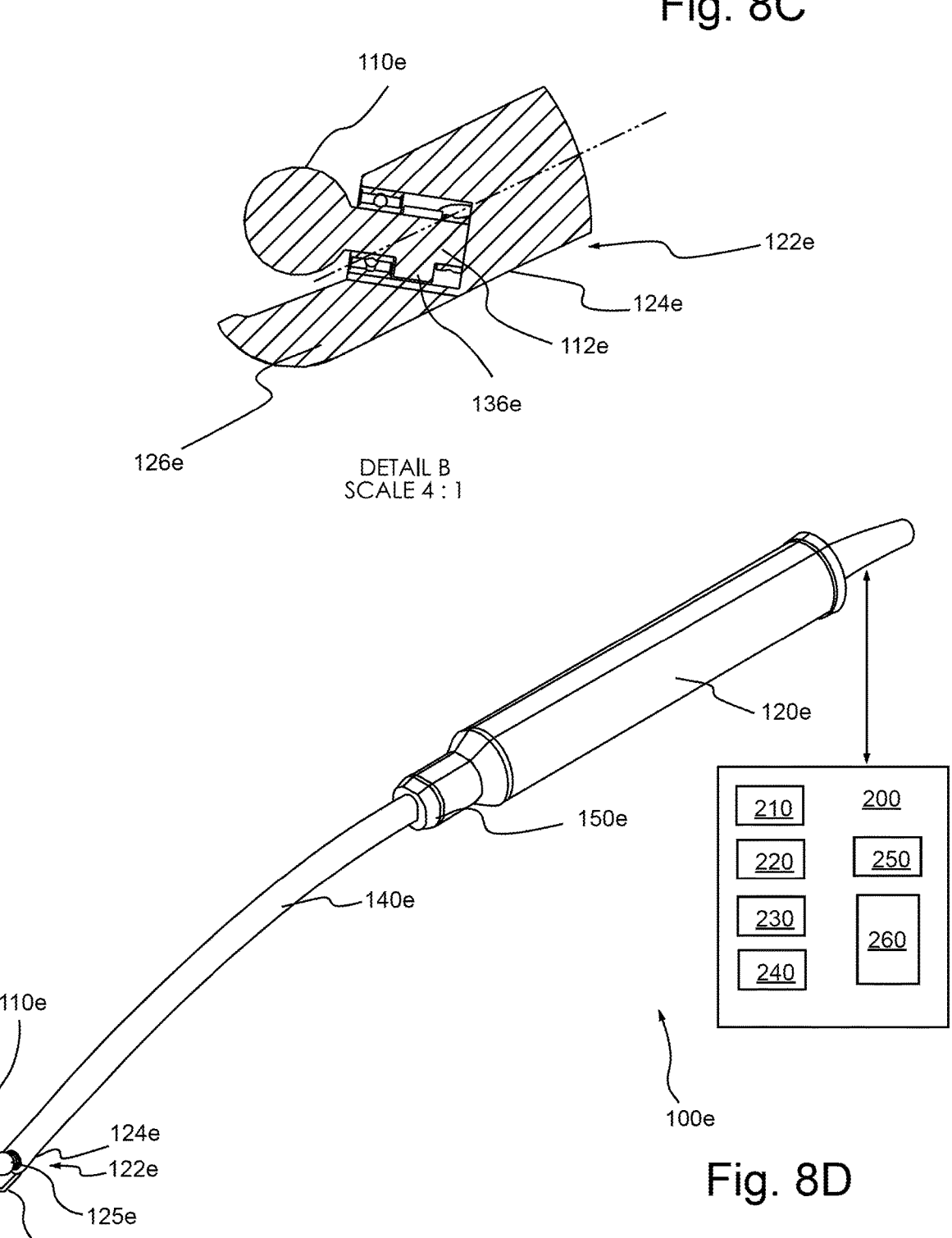
FIG. 8C illustrates an enlarge portion of the surgical drill of FIG. 8A indicated by encircled section B of FIG. 8B.
FIG. 8D illustrates an isometric view of the surgical drill of FIG. 8A.

The surgical drill systems hereof may be operated under at least partial computer control. FIG. 8D, for example, illustrates schematically electronic circuitry 200 in operative connection with surgical drill system 100*e*. Electronic circuitry 200 includes a processor system 210 (including, for example, one or more processors/microprocessors) in communicative connection with a memory system 220. One or more algorithms may be stored in memory system 220 which are executable via processor system 210 for control of surgical drill 100*e*. Electronic circuitry may, for example, further include a user interface system 230 in communicative connection with processor system 210, a communication system in operative connection with processor system 210, and a sensor system 250 in operative connection with processor system. One or more sensors of sensor system 250 may, for example, be used in a feedback control loop. A power system 260 may be provided to power electronic circuitry 200. The surgical systems hereof may be used under manual or computer-assisted manual operation or may be incorporated with in a robotic system. Base 120*e* (or other bases hereof) may, for example, be a component of or operatively connected to a robotic arm. As known in the surgical arts, optional attachments may be provided that allow use of such attachments as navigational tools when used in connection with imaging guidance computers.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A surgical drill system for use with a drill bit, comprising:
   a base,
   a drill head positioned forward of the base and being operatively connected to the base, the drill head comprising a drill bit interface to which a shaft of the drill bit is attachable so that an axis of the shaft of the drill bit extends at an angle to an orientation of the drill head at the position of the drill bit interface, wherein the drill head comprises a support, the drill bit interface being positioned on the support so that the shaft of the drill bit extends at the angle to the support at the position of the drill bit interface;
   a drive system in operative connection with the drill bit interface which is configured to rotate the drill bit about the axis of the shaft of the drill bit when connected to the drill bit interface; and
   a guard attachable to the support at a first position forward of the shaft of the drill bit, the guard extending forward from the first position to a second position beyond a forwardmost portion of the drill bit.

2. The surgical drill system of claim 1, wherein the angle is in the range of approximately 20° to approximately 100° to an axis of the support at the position of the drill bit interface, or in the range of approximately 30° to approximately 90° to the axis of the support at the position of the drill bit interface.

3. The surgical drill system of claim 1, wherein the guard is removably attached to the support or movably attached to the support.

4. The surgical drill system of claim 1 wherein the drill head is rotatable relative to the base.

5. The surgical drill system of claim 1, wherein the drill head further comprises a second member which extends forward and is spaced from the support.

6. The surgical drill system of claim 5 wherein the second member is positioned opposite the support and the drill bit is positioned between the support and the second member.

7. The surgical drill system of claim 1, further comprising an extending section that extends between the base and the support.

8. The surgical drill system of claim 7, wherein the base, the extending section, the support, and the guard define a tool shaft that extends along a longitudinal axis of the surgical drill system.

9. The surgical drill system of claim 1, wherein the guard defines a beveled edge extending to a point at the second position.

10. The surgical drill system of claim 9, wherein the guard comprises a first radial surface extending from the first position to the second position, wherein the guard comprises a second radial surface extending from the first position to a third position rearward of the second position, and wherein the beveled edge extends from the second radial surface at the third position to the first radial surface at the second position such that the beveled edge is angled relative to the first radial surface and the second radial surface.

11. A surgical drill system for use with a drill bit, comprising:
    a base,
    a drill head positioned forward of the base and being operatively connected to the base, the drill head comprising a drill bit interface to which a shaft of the drill bit is attachable so that an axis of the shaft of the drill bit extends from the drill head at the position of the drill bit interface, the drill head further comprising a guard extending forward of the drill bit interface, wherein the drill head comprises a support, the drill bit interface being positioned on the support so that the shaft of the drill bit extends from the drill head at the position of the drill bit interface;
    a drive system in operative connection with the drill bit interface which is configured to rotate the drill bit about the axis of the shaft of the drill bit when connected to the interface; and
    the guard attachable to the support at a first position forward of the shaft of the drill bit, the guard extending forward from the first position to a second position beyond a forwardmost portion of the drill bit.

12. A method of performing endoscopic surgery, comprising:
    endoscopically inserting a surgical drill system, wherein the surgical drill system comprises
    a base,
    a drill head positioned forward of the base and being operatively connected to the base, the drill head comprising a drill bit interface to which a shaft of a drill bit is attachable so that an axis of the shaft of the drill bit extends at an angle to an orientation of the drill head at the position of the drill bit interface, wherein the drill head comprises a support, the drill bit interface being positioned on the support so that the shaft of the drill bit extends at the angle to the support at the position of the drill bit interface,
    a drive system in operative connection with the drill bit interface which is configured to rotate the drill bit about the axis of the shaft of the drill bit when connected to the interface, and
    a guard attachable to the support at a first position forward of the shaft of the drill bit, the guard extending forward from the first position to a second position beyond a forwardmost portion of the drill bit; and
    advancing the drill bit in a generally forward direction into bone.

13. The method of claim 12, wherein the angle is in the range of approximately 20° to approximately 100° to an axis of the support at the position of the drill bit interface, or in the range of approximately 30° to approximately 90° to the axis of the support at the position of the drill bit interface.

14. The method of claim 12, wherein the guard is removably attached to the support or movably attached to the support.

15. A method of performing endoscopic craniosynostosis surgery on a patient, comprising:
    endoscopically inserting a surgical drill system, wherein the surgical drill system comprises
    a base,
    a drill head positioned forward of the base and being operatively connected to the base, the drill head comprising a drill bit interface to which a shaft of a drill bit is attachable so that an axis of the shaft of the drill bit extends at an angle to an orientation of the drill head at the position of the drill bit interface, wherein the drill head comprises a support, the drill bit interface being positioned on the support so that the shaft of the drill bit extends at the angle to the support at the position of the drill bit interface,
    a drive system in operative connection with the drill bit interface which is configured to rotate the drill bit about the axis of the shaft of the drill bit when connected to the interface, and
    a guard attachable to the support at a first position forward of the shaft of the drill bit, the guard extending forward from the first position to a second position beyond a forwardmost portion of the drill bit, and
    removing bone via the surgical drill system.

16. The method of claim 15 further comprising placing a component between the bone and underlying soft tissue during removal of the bone to protect the underlying soft tissue from contact with the drill bit.

17. The method of claim 16 wherein the component is a portion of an instrument, independent from the drill system.

* * * * *